(12) United States Patent
Hall et al.

(10) Patent No.: US 7,708,558 B1
(45) Date of Patent: May 4, 2010

(54) IMPLANT, METHOD FOR PRODUCING THE IMPLANT, AND USE OF THE IMPLANT

(75) Inventors: Jan Hall, Göteborg (SE); Jukka Lausmaa, Göteborg (SE)

(73) Assignee: Nobel Biocare AB (publ.), Göteborg (SE)

( * ) Notice: Subject to any disclaimer, the term of this patent is extended or adjusted under 35 U.S.C. 154(b) by 0 days.

(21) Appl. No.: 09/980,011

(22) PCT Filed: May 23, 2000

(86) PCT No.: PCT/SE00/01027

§ 371 (c)(1), (2), (4) Date: Jun. 4, 2004

(87) PCT Pub. No.: WO00/72777

PCT Pub. Date: Dec. 7, 2000

(30) Foreign Application Priority Data

May 31, 1999 (SE) .................................. 9901971

(51) Int. Cl.
 *A61C 8/00* (2006.01)
 *A61F 2/28* (2006.01)
(52) U.S. Cl. .................. 433/174; 623/23.55; 623/23.56
(58) Field of Classification Search ............. 623/23.53, 623/23.55, 23.56; 433/174
See application file for complete search history.

(56) References Cited

U.S. PATENT DOCUMENTS

| | | | |
|---|---|---|---|
| 4,330,891 A | 5/1982 | Branemark et al. | |
| 4,542,539 A | 9/1985 | Rowe, Jr. et al. | |
| 4,655,776 A * | 4/1987 | Lesinski | 623/10 |
| 4,818,572 A * | 4/1989 | Shimamune et al. | 427/327 |
| 5,164,187 A | 11/1992 | Constantz et al. | |
| 5,332,626 A | 7/1994 | Conston et al. | |
| 5,354,390 A | 10/1994 | Haszmann et al. | |
| 5,691,305 A * | 11/1997 | Baylink et al. | 514/8 |
| 6,312,472 B1 * | 11/2001 | Hall et al. | 623/23.53 |
| 6,447,550 B1 * | 9/2002 | Hunter et al. | 623/22.15 |
| 6,582,470 B1 * | 6/2003 | Lee et al. | 623/23.55 |
| 6,689,170 B1 * | 2/2004 | Larsson et al. | 623/23.53 |
| 6,730,129 B1 * | 5/2004 | Hall | 623/23.57 |
| 7,048,541 B2 * | 5/2006 | Hall et al. | 433/201.1 |
| 2005/0031663 A1 * | 2/2005 | Larsson et al. | 424/423 |

FOREIGN PATENT DOCUMENTS

| | | |
|---|---|---|
| EP | 1196110 | 7/2000 |
| WO | WO-9313815 | 7/1993 |
| WO | WO 9313815 A1 * | 7/1993 |
| WO | WO 98/48862 | 11/1998 |

* cited by examiner

*Primary Examiner*—Thomas J Sweet
(74) *Attorney, Agent, or Firm*—Connolly Bove Lodge & Hutz LLP

(57) ABSTRACT

An implant comprises or consists of titanium and has one or more surfaces which can be applied in or on a bone growth area. One or more of the said surfaces are arranged with a depot for bone-growth-initiating or bone-growth-stimulating substance, which depot is formed by a pore arrangement in a relatively thick oxide layer on the titanium. The substance is acted on, for a considerable period of time, by one or more release functions for the substance which permit a controlled or optimized release of substance to the surrounding tissue or bone growth area.

14 Claims, 5 Drawing Sheets

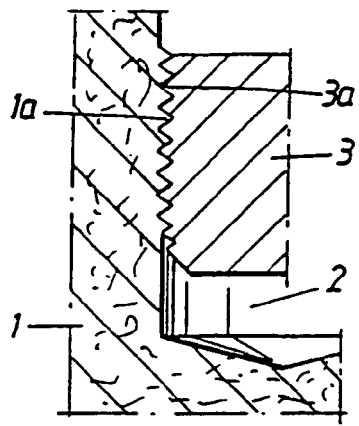
Fig. 1
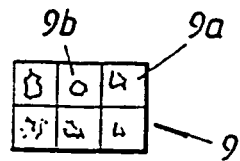
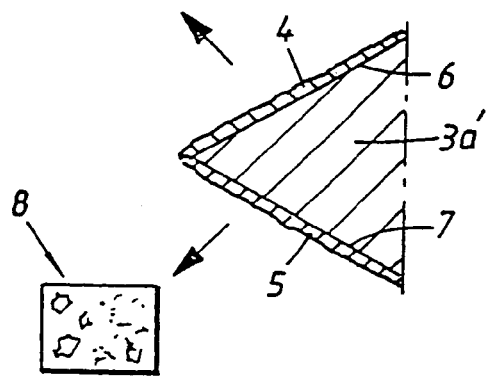
Fig. 1a
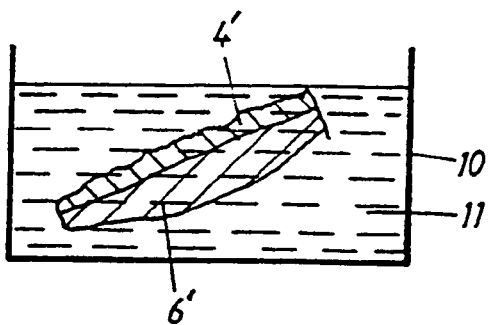
Fig. 1b
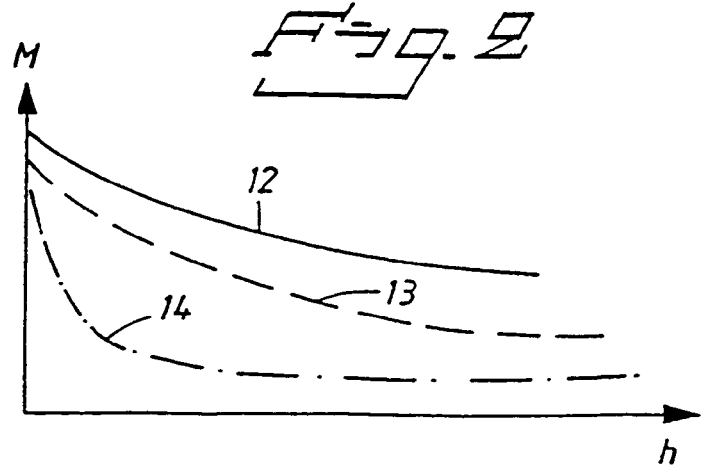
Fig. 2

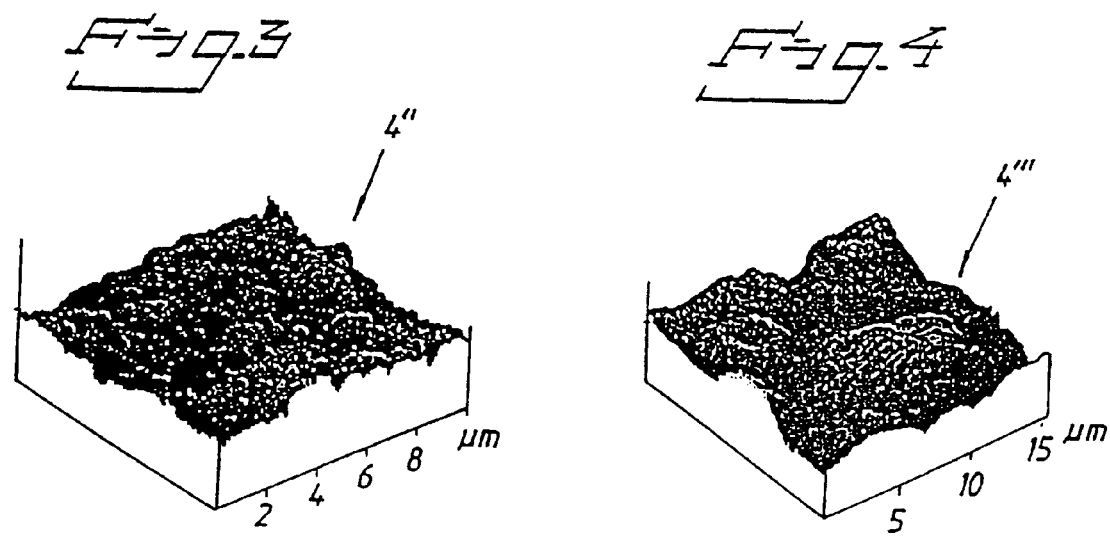
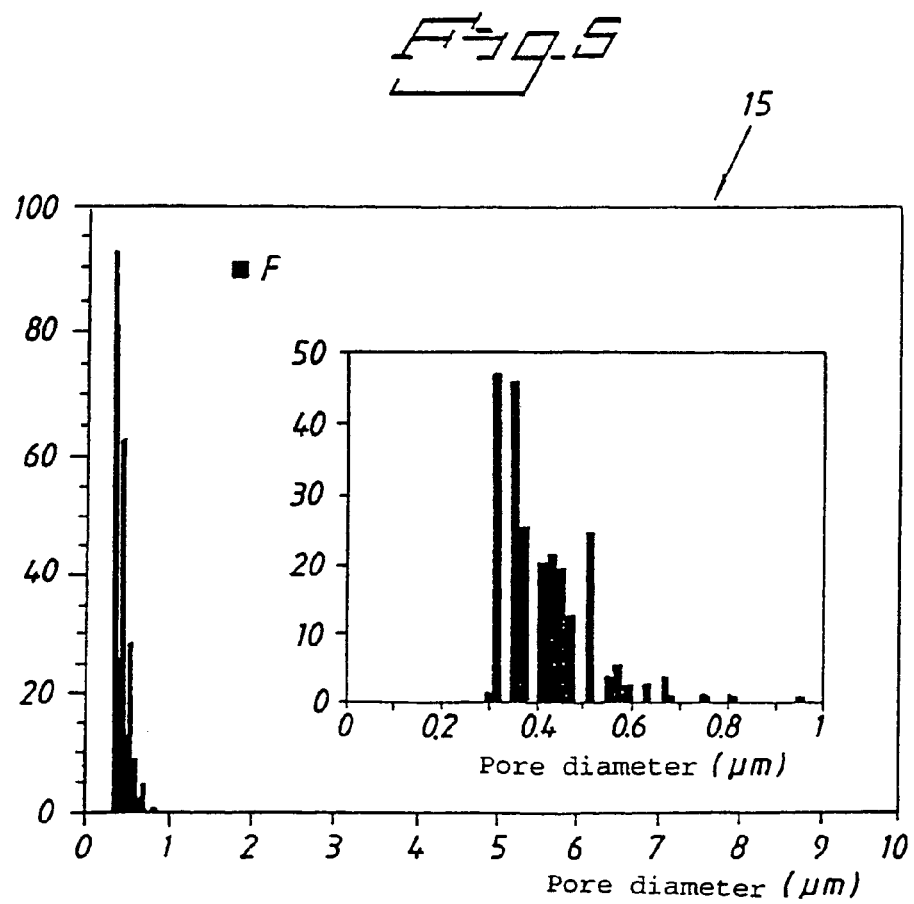

Fig. 10

| Electrolyte | U (V) | I (mA) | Time (s) | Pore diam. ($\mu m$) | Pore density ($10^8/cm^2$) | Porosity. (%) | Oxide thickness ($\mu m$) |
|---|---|---|---|---|---|---|---|
| 0.35M $H_2SO_4$ | 250 | 300 | 400 | n.a. | | | 9.2-13.5 |
| 0.35M $H_2SO_4$ | 250 | 800 | 300 | n.a. | | | 19.1-21.3 |
| 1.0M $H_2SO_4$ | 200 | 200 | 400 | n.a. | | | 5.8-6.5 |
| 0.35M $H_2SO_4$ +160 min. | 200 | 200 | 300 | 0.28-0.92 | 0.45 | 5.65 | 3.5-7.0 |
| 0.35M $H_2SO_4$ etched | 200 | 200 | 300 | 0.06-0.43 | 2.48 | 6.47 | 2.2-2.8 |
| 0.15M $H_2SO_4$+ | 300 | 200 | 300 | 0.31-2.27 | 0.078 | 4.16 | 2.9-6.5 |
| 0.25M $H_2SO_4$+ | 300 | 200 | 300 | 0.31-2.65 | 0.080 | 7.84 | 3.6-6.5 |
| 0.35M $H_2SO_4$+ | 300 | 1400 | 300 | 0.31-4.06 | 0.060 | 10.69 | 3.6-11.0 |

US 7,708,558 B1

IMPLANT, METHOD FOR PRODUCING THE IMPLANT, AND USE OF THE IMPLANT

TECHNICAL FIELD

The present invention relates to an implant which can be used in dentistry, for example. The implant comprises or consists of titanium and has one or more surfaces which can be applied in or on one or more bone growth areas. One or more of the said surfaces are arranged with a depot for bone-growth-initiating or bone-growth-stimulating substance TS, for example BMP (e.g. type 2 or type 4), where BMP stands for Bone Morphogenetic Proteins, and which depot is formed by a pore arrangement in a relatively thick oxide layer on the titanium.

The invention also relates to an implant for application in a hole formed in bone, for example the jaw bone. It also relates to a method for producing an implant intended to be applied in a hole of the said type. The invention also concerns the use of a highly porous and thick titanium oxide layer to which a bone-growth-initiating and/or a bone-growth-stimulating substance, preferably in the form of BMP, has been added.

The invention also relates to a method for producing, on an implant comprising or consisting of titanium, and by means of anodic oxidation, relatively thick oxide layers on one or more titanium surfaces which are intended to be placed against or arranged adjacent to one or more bone growth areas. At least part or parts bearing the said surface or surfaces is/are intended to be prepared and immersed in electrolyte, and the implant is brought into contact with an electrical energy source above the electrolyte surface, and the oxidation process is established by also connecting to the energy source a counter-electrode which is arranged in the electrolyte.

PRIOR ART

It is already known that, under certain conditions, implants made of commercially pure (99.6%) titanium permit incorporation of surrounding bone tissue so that intimate contact can be obtained between implant and tissue. The intimate contact between the implant and normal bone tissue, often referred to as osseointegration, in turn permits good and permanent anchoring of the implant, which can be used in various clinical treatment situations. Titanium implants anchored in bone can be used as securing elements for tooth replacements and tooth prostheses, or for other types of prostheses or devices (cf. finger joints, prosthetic eyes, prosthetic ears, hearing aids). The reason for the good bone incorporation results which are achieved in particular with titanium implants produced by turning or milling can be seen to lie in the favourable combination of structure (topography and surface roughness) and chemical compositions to which the manufacturing method gives rise. In this connection, reference may be made to Swedish Patent 7902035-0. The above-mentioned titanium surfaces typically have a surface roughness (Ra) in the range of 0.1-1 µm. The chemical composition of the surface is essentially titanium dioxide ($TiO_2$) which is present in the form of a thin (<10 nm) oxide layer. The surface is also indicated as having a porosity in the range of 10-1000 nm. If the pore density of the previously known surfaces is studied more closely under a scanning electron microscope, it emerges that the pore density of these surfaces is relatively low, and that the pore depth in the oxide can never exceed 10 nm.

A number of experimental studies have been conducted in order to investigate bone incorporation around types of titanium surfaces other than those which have been turned or milled. In these studies, different surface preparation methods have been used to modify various properties, such as surface topography, oxide thickness, surface composition, etc., of the titanium surfaces. Examples of methods which may be used for modifying the surface topography of titanium implants are: sand-blasting, plasma spraying, particle sintering, electro-polishing, and anodic oxidation. The results from these studies show that the surface topography at different levels can affect bone incorporation and the mechanical anchoring of the implant, both in terms of quality and quantity, cf. the said patent specification. It has been shown, for example, that threaded titanium implants with sand-blasted surfaces and with surface roughness (Ra) at the micrometer level can give rise to higher twisting forces than surfaces which have only been turned or milled. It has also been demonstrated that certain types of electrochemically modified titanium surfaces can give rise to more rapid bone incorporation than the titanium surfaces which have been turned or milled. The reason for this improvement probably lies in a combination of a more favourable surface topography and a greater oxide thickness. The last-mentioned surfaces can be considered to be heterogeneous and consist essentially of smooth areas with a relatively dense oxide ($TiO_2$), and a minority of the areas having a surface roughness and a certain oxide porosity at the level of about 1 µm. The increased oxide thickness of these surfaces, about 200 nm, can be expected to result in an improved corrosion resistance of the material, and thus a favourable effect on account of the lower rate of titanium ion release.

Against the background of the known facts set out above, it is thus possible to advance the hypothesis that a high oxide porosity and high oxide thickness can have a positive effect on the rate of bone incorporation around titanium implants. It is also known that the biological processes surrounding incorporation in connection with the said implants can be influenced by using various types of substances. Thus, it is known that the rate at which bone is formed can be affected to a large extent by growth factors which are produced by means of substances which initiate or stimulate bone growth. Examples which may be mentioned are substances belonging to the super-family TGF-β, and other bone matrix proteins.

It is known per se to produce different types of porous surfaces or layers from titanium-based material. Reference may be made, inter alia, to the article published by Dunn et al. and entitled "Gentamicin sulfate attachment and release from anodized TI-6A1-4V orthopedic materials" in "Journal of Biomedical Materials Research, Vol. 27, 895-900 (1993)".

In this article, general reference is made to the fact that it is possible to produce porous titanium and oxide layers using so-called anodic oxidation, which is an electrochemical process. In this connection, it is proposed that the layer or layers be used as a depot or store for antibiotic substances.

Reference may also be made to the article "Formation and characterization of anodic titanium oxide films containing Ca and P" by Hitoshi Ishizawa and Makoto Ogino in "Journal of Biomedical Materials Research, Vol. 29, 65-72 (1995)". This article shows that it is already known to use an electrochemical process to produce relatively thick titanium oxide layers provided with a pore arrangement which gives the layers a highly porous structure. It is also mentioned in this connection that the layers can be used as supports for substance for rapid bone growth.

Porous surface layers have thus previously been produced on titanium surfaces intended as implant material. In most cases, however, the aim of this preparation has been other than that concerned in the present invention. Thus, it has previously been proposed to develop calcium-containing and phosphorus-containing oxide layers which, by means of further treatment, can be made to precipitate hydroxyapatite crystals on the oxide layer. Reference may also be made to U.S. Pat. Nos. 4,330,891 and 5,354,390 and to European Patent Specification 95102381.1 (676 179).

DESCRIPTION OF THE INVENTION

Technical Problem

In implants of the type in question here, there is a need to achieve shorter incorporation processes between bone and implant, especially in the case of soft bone structures or bone qualities. The properties of the titanium material and of the growth substance must be used as far as possible to achieve this. The invention is based, inter alia, on this problem.

It is known per se to use implants with a screw connection to be anchored in the jaw bone. In this regard, it is known that the quality of the jaw bone can vary considerably. In the inner parts of the jaw bone in particular, the bone material can be extremely soft and/or present relatively thin trabeculae. In such cases, it is preferable to be able to effect reliable implant attachments. The invention also solves this problem and proposes effective implants and methods for anchoring the implants in soft bone material too.

In connection with the invention, methods are used for producing the relatively thick and porous material. In this regard, it is important that clear and effective methods can be used. The invention solves this problem too.

Previous methods and arrangements were based on the problem of bone growth on the implant, and less consideration was given to the interaction between the implant and the bone material in question. It is important to establish an effective bioactive surface between the implant and the dentine or equivalent bone. The invention solves this problem too.

It is also important to achieve an effective formation of substance in the porous surface or the structure which is to function as a depot for the growth substance in question. The invention solves this problem too.

It is of great advantage that the porous structure functioning as depot for growth-initiating or growth-stimulating substance can intervene, in a controlled manner, in the release of the substance during a desired or predetermined period of time. It can thus be advantageous to have a better controlled substance release during a certain time span which can be chosen depending on the case in question. The invention solves this problem too.

It is of great advantage in practice to be able to advance the implant technique a further stage in the technical field, where the practical application uses bioactive surfaces instead of simply the properties of the titanium material itself, as was previously the case. By stimulating bone growth in connection with implants, it is possible, in the field of dentistry, among others, to create possibilities for controlling and improving the problems of incorporation. The invention solves this problem too.

It has been shown that one can expect effective incorporation processes in connection with implants for application in holes made in bone, primarily in the jaw bone. By delivering one or more bioactive substances directly into a surrounding tissue or bone environment which is to be strengthened, stimulation factors can be effectively achieved. The invention is intended in particular to solve this problem too.

Implants for holes made in the jaw bone are in most cases provided with one or more threads via which the implant is to be mechanically anchored in the hole by means of screwing. Providing a certain degree of irregularity on the surface structure which is to be screwed in imposes requirements in terms of greater screwing forces, which in themselves must not counteract the support function for the bioactive substance. The invention solves this problem too.

It is known that the jaw bone status varies considerably from one case to another and that, in the case of soft and/or thin jaw bone, it is important to be able to create arrangements which strengthen the bone growth in these areas. The invention aims to solve this problem too.

To create a high degree of porosity in the oxide layer in question, it is important to use the correct oxidation processes. These can be crucial in determining whether or not one succeeds in achieving the desired results. The invention solves this problem too.

Solution

The feature which can principally be regarded as characterizing an implant according to the invention is that the substance, for a period of time which can be between 1 and 2 weeks, for example, is acted on by one or more release functions which permit a controlled or optimal release of substance to the respective surrounding tissue or tissue/bone growth areas. If the incorporation function or bone growth function is promoted by this, other substance release processes can also be established.

In one illustrative embodiment, the implant works with more than one, i.e. two or more, release arrangements which are produced by means of different pore arrangements within one or more areas of one or more of the initially mentioned surfaces. Pores with different pore characteristics can be used. Thus, for example, open or more or less closed pores, different pore depths, different pore densities, etc., can be arranged within one or more areas of the said surfaces. The different areas can also be provided with different pore characteristics.

It is also important that the oxide layer on the titanium is composed in an advantageous manner. In one embodiment, the surface of the oxide layer will comprise about 20% titanium, about 55% oxygen and about 20% carbon. The oxide layer as such will be highly porous.

In a preferred embodiment, the implant is of the type which comprises one or more threads. The implant will bear the said oxide layers or surfaces at least in connection with the said threads.

In a preferred embodiment, the oxide layer has a surface roughness of about 1-5 µm or less, and has a thickness preferably in the range of 2-10 µm. The oxide layer must be highly porous, with pore diameters in the range of 0.01-10 µm.

Another feature which can principally be regarded as characterizing an implant is that it comprises a titanium portion which can cooperate with a hole formed in a bone, and that the titanium portion is designed with one or more very thick titanium oxide layers having surfaces which can be placed against the bone in the hole formation. Further characteristics are that each oxide layer is provided with a pore arrangement which functions as a depot for bone-growth-initiating and/or bone-growth-stimulating substance, and that, when the depot is filled with substance and the implant is in position in the hole, a release function for releasing the substance to the surrounding tissue or bone comes into operation.

The release function can be controlled for a chosen, essentially protracted period of time. The release function can be controlled by the choice of pore arrangement and pore characteristics in or on the said layer.

The feature which can principally be regarded as characterizing a method according to the invention is that the implant is produced, for example by means of machining, with a portion made of titanium which has surfaces which can be placed against the bone when the implant is in position in the hole. The said titanium on the said surface or surfaces is subjected to anodic oxidation to an extent which gives a highly porous and relatively thick oxide layer on each surface concerned. A bone-growth-initiating or bone-growth-stimulating substance TS, which can be BMP, is applied to the said porous and thick layers, for example by saturation or by immersion in or dropping on and/or painting on of the substance. The implant is placed in its position in the hole, resulting in the process of release of the substance to the bone being started upon insertion, the process being triggered by components in the tissue and/or bone.

In one embodiment, the implant, at the part or parts bearing the said surfaces, is provided with one or more threads, via which the implant is screwed into the bone. In one embodiment, the oxidized layer and its associated pore system are immersed for a chosen time, for example 1 hour, in a container holding the substance, so that effective penetration of the substance into the porous layer takes place.

The novel use according to the invention is characterized in that the highly porous and thick titanium oxide layer, to which bone-growth-initiating or bone-growth-stimulating substance has been added, is used on implants which can be inserted into holes in bone, preferably the jaw bone.

In a preferred embodiment, the use is characterized in that the porous layer with added substance is used on implants with thread or threads, joint implants, etc.

Another feature which can principally be regarded as characterizing an implant according to the invention is that the oxide layer has a thickness in the range of 1-20 μm, preferably 2-20 μm. In a preferred embodiment, the oxide layer has a surface roughness in a range of 0.4-5 μm. In a further preferred embodiment, the oxide layer is highly porous, with a pore number of $1 \times 10^7$-$1 \times 10^{10}$ pores/cm$^2$. Each surface essentially has pores with diameter sizes in the range of 0.1-10 μm. The total pore volume is preferably within the range of $5 \times 10^{-2}$ to $10^{-5}$ cm$^3$.

A method for carrying out the above-mentioned anodic oxidation can principally be regarded as being characterized by the fact that diluted inorganic acids and/or diluted organic acids and/or small quantities of hydrofluoric acid or hydrogen peroxide are added to the electrolytic composition, and the energy source is chosen to operate at a voltage value or voltage values in the range of 150-400 volts.

In one embodiment, the voltage can be varied for the same implant at different times in order to create different pore sizes within the same surface areas. In addition, the position of the implant in the electrolyte can be changed, together with the composition of the electrolyte and/or the voltage, in order to create areas with different layer thicknesses, porosities or pore characteristics on the implant.

ADVANTAGES

By means of what has been described above, a new dimension in implantation techniques is achieved, especially in the area of dentistry. Earlier clinical trials which opened up the way to using bioactive substances can now be given practical application, especially in connection with holes made in bone of low quality with respect to hardness and of low quantity. The invention affords particular advantages in the case of implants applied in holes made in the jaw bone, where the bioactive substance can be given controlled diffusion functions (concentration diffusions) into the surrounding bone material. The incorporation and bone growth period can be controlled and enhanced by a combination of the titanium material itself, the geometrical shape of the implant, and the bioactive substance. Economically advantageous methods can be established on the market, and prepared implants and packages can be made commercially available. Alternatively, the substance and the implant (with its specific porous oxide layer character) can be made available separately and then assembled in situ according to instructions.

DESCRIPTION OF THE FIGURES

A presently proposed embodiment of an arrangement, method and use according to the invention will be described below with reference to the attached drawings, in which:

FIG. 1 shows, in vertical section, parts of a threaded implant anchored by screwing in a jaw bone, FIG. 1a shows, in vertical section and with partial surface enlargement, a thread of the implant according to FIG. 1, with an oxide layer having been established on the thread surface, FIG. 1b shows from the side, and in vertical section, part of the implant according to FIGS. 1 and 1a which has been partially immersed in bioactive substance, the porous layer being saturated with the substance in question, FIG. 2 shows, in diagram form, the release function for bioactive material deposited in the oxide layer, FIG. 3 shows, in perspective, and in a greatly enlarged view, parts of a porous titanium oxide layer on an implant according to FIG. 1, FIG. 4 shows, in perspective, parts of a second porous titanium oxide layer according to FIG. 1, FIG. 5 shows, in diagram form, the pore diameter sizes and the pore number in the layer according to FIG. 3, FIG. 10 shows, in table form, parameters of the titanium oxide layer.

DETAILED EMBODIMENT

Figure 6:
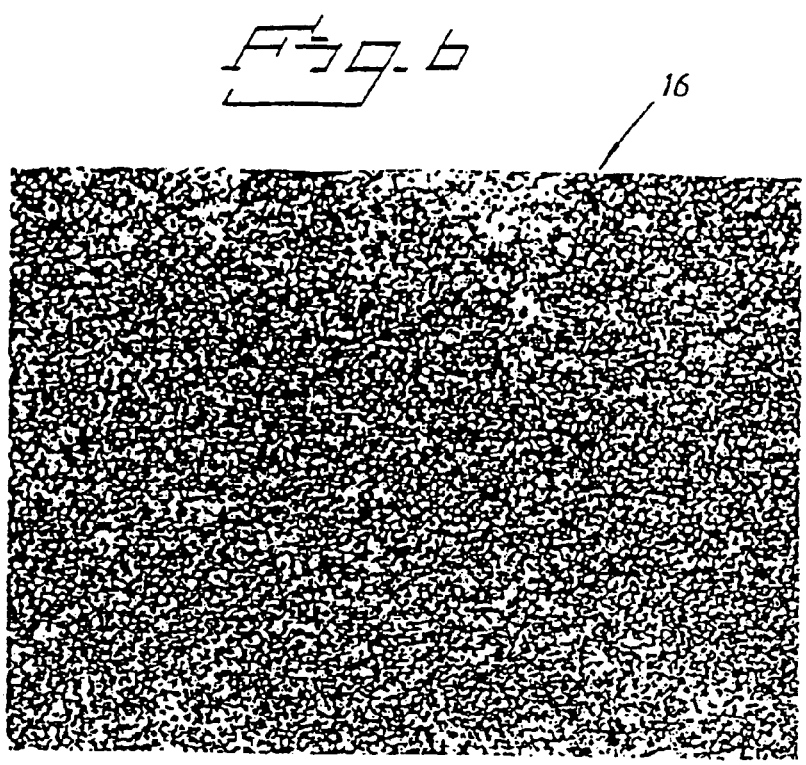
FIG. 6 shows, from above, a first embodiment of the pore character of the oxide layer, produced using a combination of electrolyte, oxidation energy and time.

In accordance with what has been described above, the present invention proposes, inter alia, a method by which it is possible to establish a high oxide porosity and oxide thickness on a titanium implant in order to function as a support for a substance which initiates, stimulates and increases the rate at which the implant incorporates in the bone material in question in the human body. The invention is based on the recognition that the rate at which bone forms can to a large extent be influenced by growth factors which are produced using, for example, TGF-β and other bone matrix proteins. The invention aims, inter alia, to deliver and release such substances in a controlled manner to the bone surrounding the metal implant. The oxide layer has a high degree of porosity. The pore volumes function as depots for the substances. The relatively large surface area of the pore walls is used to immobilize the substances through adsorption. According to the invention, the implant surface is made of a highly porous titanium oxide which itself has positive properties in respect of incorporation. In order to control the rate of release of the active substances, the present invention proposes that the pore density (i.e. the number of pores per surface unit) and the pore geometry (diameter and depth) are varied in a controlled manner.

Among other things, the present invention concerns a surface layer on a titanium implant which is designed so that its properties themselves have a positive effect on bone incorporation around the implant and in addition have the function of constituting a support for an effective substrate which is delivered in a controlled manner to the implant surface in order then to release biologically active substances which accelerate the formation of bone around the implant. The surface consists of an oxide layer which largely comprises $TiO_2$ and has a surface roughness Ra preferably in the range of 1-5 µm (for example 4 µm) or less. In addition, the oxide layer will have a thickness which, in one embodiment, can be varied within a range of 1-20 µm. In exceptional cases, it will be possible to use values of as little as 0.5 µm. The oxide layer will also be highly porous, with a large number of open pores per surface unit, and with pore diameters which can be varied in the range of 0.01-10 µm. In a preferred embodiment, the oxide layer has a thickness in the range of 2-20 µm. In a further embodiment, the oxide layer has a surface roughness in the range of 0.4-5 µm. In the said preferred embodiment, the oxide layer is highly porous, with $1\times10^7$-$1\times10^{10}$ pores/$cm^2$. The implant in the preferred embodiment will also have pores with diameter sizes in the range of 0.1-10 µm. The pore volume is chosen in accordance with the above. This arrangement will be able to be combined with pores which have different characteristics, smaller diameters, more or less closed configurations, and different depths. The resulting porous oxide layer gives rise to two main effects in implant applications in bone. First, the properties of the surface themselves may be expected to result in accelerated incorporation of bone and anchoring of the implant by means of the preferred combination of surface roughness, pore volume, porosity and oxide thickness. In addition, as a second effect, the surface layer can function as a suitable means of immobilizing controlled quantities of biologically active substances which act on the growth process in the bone. The surface layer thus functions as a support for the substance in question. The immobilization can be effected in principle in different ways, the first being achieved by spontaneous adsorption of molecules in the solution in question onto the surfaces of the pore walls. In a second embodiment, use is made of the fact that the substances in question have a net charge different from zero, which means that adsorption from solution onto the surfaces of the pore walls can be accelerated by means of an electrical field which has been applied by applying a suitable voltage to the sample in a cell. A third way is to press the substances into the pores by pressure, the substance in question being given a suitable viscosity. A fourth way to apply substance is to use a gel support for the substance. The gel support with the substance is applied on or pressed against the porous oxide layer. The gel support is of a highly viscous type. The release or the release function for the substance into the tissue will depend on the geometric configurations of the pores. By controlling the pore geometries or the pore characteristics, different rates of release can be obtained. By different combinations of smaller and larger pores, the release can be programmed to follow a desired sequence over the course of time. This is due to the fact that a high rate of release is obtained in the initial stage from larger pores, and this is followed by slow or slower release, for a longer period of time, from small and/or deep pores.

In FIG. 1, reference number 1 indicates parts of a jaw bone in which a hole 2 has been formed. An implant 3 has been screwed into the hole 2 via its threads 3a. The said threads produce a corresponding thread formation 1a in the jaw bone as the implant is screwed into the hole. Alternatively, the hole can be pre-threaded.

FIG. 1a shows the surface character of a thread 3a' on a very greatly enlarged scale (for the sake of clarity). Reference numbers 4 and 5 indicate oxide layers on surfaces 6 and 7 of the thread part 3a'. The thread or threads is/are turned or milled and, if appropriate, polished or subjected to another form of machining. The implant 3, 3a' in the present case is assumed to be made of titanium, and the said layers 4 and 5 are titanium oxide layers which are produced in the manner described below. FIG. 1a shows a first area 8 of the surface 7. The area in question can comprise pores with different pore sizes, pore depths, etc., in accordance with what has been described above. FIG. 1a also shows a second partial enlargement 9 of the surface 6. The different areas 9a and 9b of area 9 can be provided with different pore characters.

In FIG. 1b, reference number 10 indicates a container for substance 11 in accordance with what has been described above. In the container, parts of the surface 6' and the titanium oxide layer 4' are shown immersed in the substance 11. Upon immersion in the substance 11, substance penetrates into the porous layer 4' which thereafter, when the implant is removed from the container, functions as a depot or store for the substance which has thus penetrated into it. The immersion or adsorption time is chosen as a function of the configuration of the porous layer. In one embodiment, the layer 4' will, for example, be immersed in the substance for 1 hour (see also description below).

FIG. 2 shows different controlled release functions with curves 12, 13 and 14. The curve 12 shows a first release function during a time period which can be chosen to last 1 to 2 weeks. Other courses for the release function can be chosen, as shown by the curves 13 and 14, where the curve 13 decreases more than the curve 12, and where the curve 14 shows an initially powerful release function which decreases relatively quickly. The choice of release function or curve shape can be chosen on the basis of experience of the bone growth process. The first curve shows a relatively slowly decreasing release function.

FIGS. 3 and 4 show different titanium oxide layer structures 4'' and 4'''. In the structure 4'', the surface has diffraction peaks deriving from the crystal structure for rutile and underlying titanium. The structure 4''' according to FIG. 4 has diffraction peaks from the crystal structure for a mixture of anatase, rutile and underlying titanium. The oxide layers according to FIGS. 3 and 4 have somewhat different relative concentrations. Thus, the surface of the oxide layer according to FIG. 3 has a composition of 21.1% Ti, 55.6% and 20.6% C. In addition, there are small amounts of S (0.8%), N (1.4%) and P (0.6%). The composition of the oxide layer according to FIG. 4 is 21.3%, 56.0% and 20.5% respectively (and 0.8%, 0.7% and 0.6% respectively). The number of pores in the oxide layers shown can be in the range of $187.6\times10^6$. A total pore volume or porosity can be chosen at around $21.7\times10^{-5}$ $cm^3$. The oxide layers can be saturated in substance, with saturation times of up to 48 hours, for example.

FIG. 5 is intended to show, at 15, the pore diameters used in the titanium oxide layer according to FIG. 3. This shows the number of pores with diameters in the range of 0.1-0.8 µm.

Figure 7:
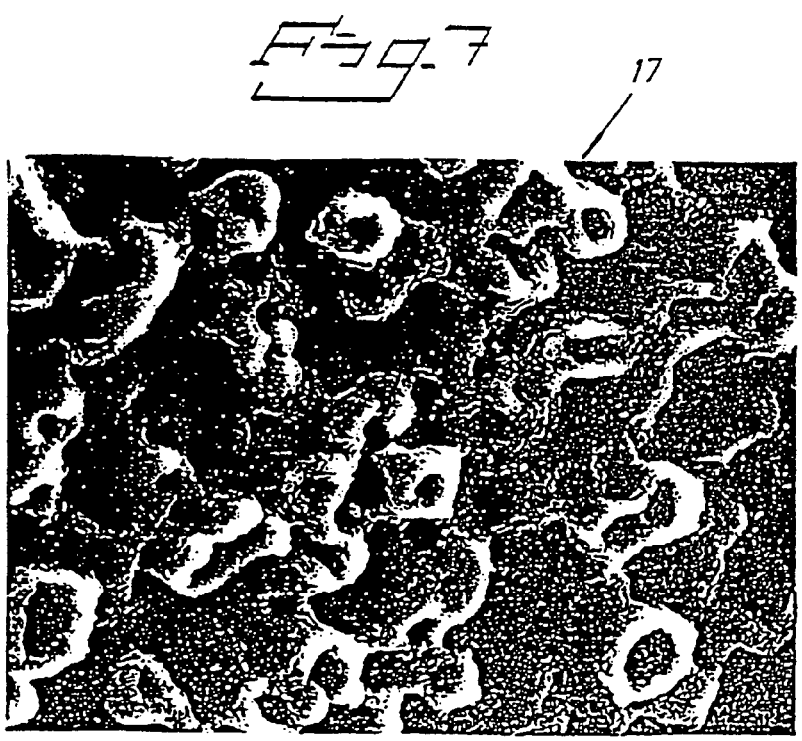
FIG. 7 shows, from above, a second embodiment of the pore character of the titanium oxide.

FIGS. 6 and 7 show different embodiments of pore characteristics or pore structures 16 and 17.

Figure 8:
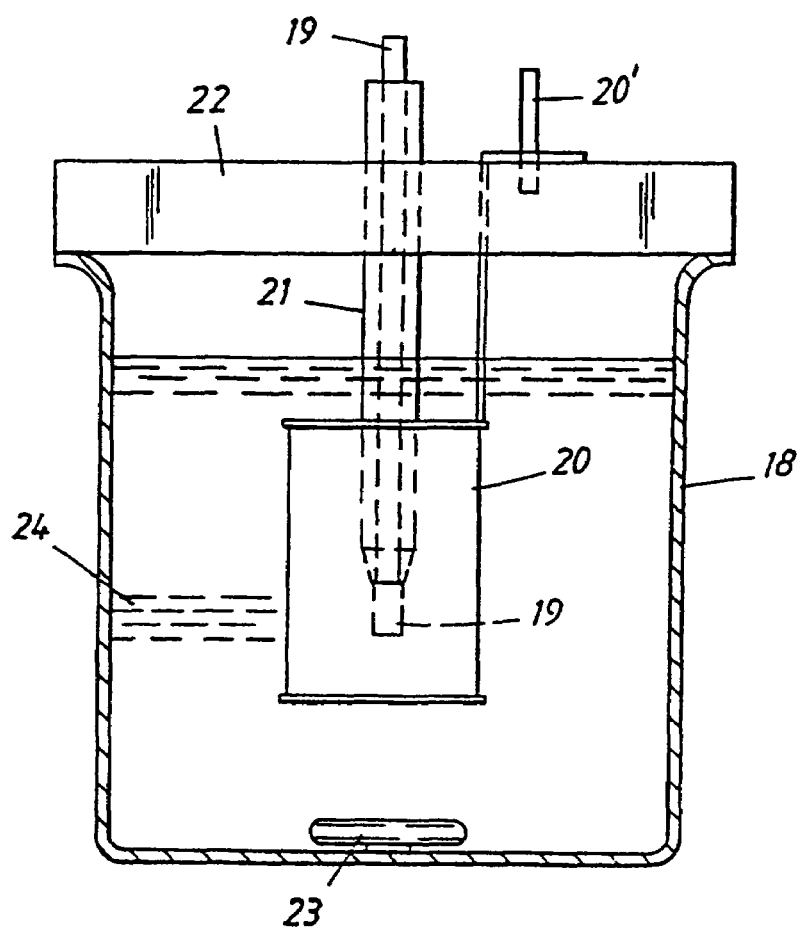
FIG. 8 shows a side view of equipment for anodic oxidation of an implant according to FIG. 1.

The titanium oxide layers according to the above are preferably produced by so-called anodic oxidation, which is an electrochemical process. The principle and procedure for obtaining the layers in question are described with reference to FIGS. 8 and 9. In FIG. 8, a container is indicated by 18. A titanium anode is indicated by 19, and a porous meshed cathode is shown by 20. A Teflon insulation for the titanium anode is shown by 21, and the anodes extend through a Teflon cover 22. A magnetic agitator 23 is also included. The connections for the anode and the cathode are indicated by 19' and 20', respectively. The implant or the parts of the implant to be prepared is/are preferably mechanically worked by turning, milling, polishing, etc. The implant or the parts in question comprise(s) titanium surfaces which are to be treated in the electrochemical process. The implant or the parts in question is/are mounted on a holder which is immersed in a bath of electrolyte 24 in the container. The parts of the implant which are not to be treated are masked with a liquid-tight protective cover or alternatively with a suitable lacquer which is applied on those parts in question which are not to be treated. The implant or its said parts is/are in electrical contact, via the holder, with the connection 19 above the electrolyte surface. In the electrolyte, the said cathode 20 serves as a counter-electrode. This counter-electrode is made of a suitable material, for example Pt, gold or graphite. The counter-electrode is preferably mounted on the holder in such a way that the whole arrangement is jointly fixed in the electrolyte bath 24. The anodic oxidation is effected by applying an electrical voltage between the implant/implant part/implant parts and the counter-electrode, whereupon the implant or its part or parts in question is/are given a positive potential. The implant, the implant part/implant parts, the counter-electrode and the electrolyte constitute an electrochemical cell in which the implant or its respective part forms an anode. The difference in electrical potential between implant/implant part and counter-electrode gives rise to a current of negatively (positively) charged electrolyte ions to the implant/implant part (counter-electrode). If suitable electrolyte has been chosen, the electrode reactions in the cell result in oxide layers forming on the surface of the implant or implant part. As the electrode reactions also result in gas formation, the electrolyte should be stirred in a suitable manner, which is done using the said magnetic agitator 23 which prevents gas bubbles from remaining on the electrode surfaces.

The formation of the titanium oxide layer and its final properties are influenced by a number of parameters in the process, for example the electrolyte composition and temperature, the applied voltage and current, the electrode geometry, and the treatment time. The way in which the desired layers are produced is described in more detail below. Examples are also given of how the process parameters affect various properties of the oxide layers and how oxide thickness and porosity can be varied.

The desired layer properties are achieved starting out from mechanically worked surface, which can be turned or polished. The surface is cleaned in a suitable manner, for example by ultrasound cleaning in organic solvents in order to remove impurities from previous production stages. The cleaned implant or the cleaned implant part is secured in the said container, which is secured together with the counter-electrode on the holder. The arrangement can then be lowered into the electrolyte. The two electrodes are then coupled to a voltage source (not shown) and an electrical voltage is applied, whereupon the process starts. The process is ended after the desired time by interrupting the voltage supply.

The electrical voltage can be applied in different ways, cf. also FIG. 10. In a galvanostatic process, the current is kept constant, and the voltage is allowed to vary according to the resistance in the cell, whereas, in a potentiostatic process, the voltage is kept constant and the current is allowed to vary. The desired layers are preferably formed using a combination of galvanostatic and potentiostatic control. Galvanostatic control is used in a first stage, the voltage being allowed to increase to a preset value. When this voltage value is reached, the process changes over to potentiostatic control. On account of the resistance of the oxide layer which has formed, the current drops in this state.

Figure 9:
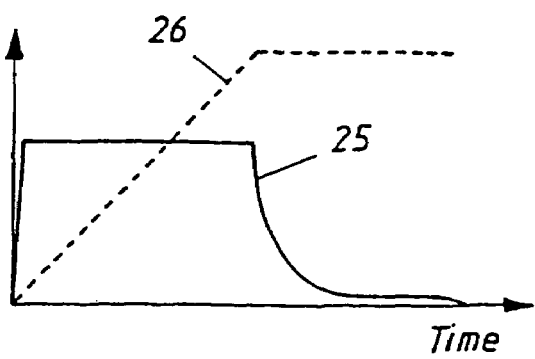
FIG. 9 shows, in diagram form, the voltage and current functions used in association with the oxidation process according to FIG. 9.

FIG. 9 shows the development of current 25 and voltage 26 over the course of time. The exact appearance of the curves depends on various process parameters and also reflects the formation of the oxide layer and its properties.

Up to a certain voltage, which is dependent on electrolyte, relatively thin (<0.2 μm) oxide layers are obtained, the oxide layer thickness being approximately linearly dependent on the applied voltage, independently of the treatment time after the maximum voltage has been reached. These layers are essentially closed, and only in exceptional cases do they have a partially open porosity. For most electrolytes, the critical voltage is around 100 volts.

To achieve the desired porous oxide layers, much higher voltages need to be applied, typically of 150 to 400 volts, depending on the electrolyte. At these voltages, the oxide thickness is no longer linearly dependent on the voltage, and much thicker layers can be produced. For certain electrolytes, the oxide thickness at these voltages is also dependent on the treatment time after the maximum voltage has been reached. Suitable electrolytes for achieving porous layers by this method are diluted inorganic acids (for example sulphuric acid, phosphoric acid, chromic acid), and/or diluted organic acids (for example acetic acid, citric acid) or mixtures of these.

FIGS. 6 and 7 show examples of porous oxide layers produced according to the above method, at 200 volts in 0.35 molar sulphuric acid and, respectively, 300 volts in 0.25 molar phosphoric acid.

The implant which has been treated in sulphuric acid has a surface with a high density of open pores. Some 20% of the surface consists of pores, with sizes (diameters) preferably in the range of 0.1-0.5 μm. The thickness of the layer is 2 μm. The implant which has been treated in phosphoric acid has a similar pore density. The pore size distribution can differ considerably. Pore sizes can be chosen preferably in the range of 0.3-0.5 μm, but a good number of larger pores (up to 1.5 μm) can also be present on the surface. The oxide thickness of this sample is 5 μm. The implant surface in question can additionally or alternatively be pretreated chemically, for example with hydrogen fluoride (HF).

The table in FIG. 10 shows the structures of oxide layers made using different process parameters.

The invention is not limited to the embodiment described above by way of example, and instead can be modified within the scope of the attached patent claims and the inventive concept.

The invention claimed is:

1. An implant for application in a hole formed in bone comprising:
    titanium and having one or more surfaces which can be applied in or on tissue areas and/or bone growth areas, one or more of the said surfaces being arranged with a depot for a bone-growth-initiating substance or bone-growth-stimulating substance of the superfamily TGF-β,
    wherein the depot is formed by a pore arrangement in a relatively thick titanium oxide layer on the titanium,
    wherein the titanium oxide layer has a thickness in the range of 1-20 μm, and wherein the depot comprises a bone-growth-initiating or bone-growth-stimulating substance of the superfamily TGF-β.

2. The implant according to claim 1, wherein the titanium oxide layer has a surface roughness in a range of 0.4-5 μm.

3. The implant according to claim 1, wherein the titanium oxide layer is highly porous, with $1\times10^7$-$1\times10^{10}$ pores/cm$^2$.

4. The implant according to claim 3, wherein the titanium oxide layer has a surface roughness in a range of 0.4-5 μm.

5. The implant according to claim 3, wherein each surface essentially has pores with diameter sizes in the range of 0.1-10 μm, and/or in that the total pore volume is within a range of $5\times10^{-2}$ and $10^{-5}$ cm$^3$.

6. The implant according to claim 3, wherein the titanium oxide layer has a thickness in the range of 2-20 μm.

7. The implant according to claim 3, wherein the titanium oxide layer is highly porous, with pore diameters in the range of 0.01-10 μm.

8. The implant according to claim 3, wherein the titanium oxide layer has a surface roughness of about 1-5 μm.

9. The implant according to claim 3, wherein the implant is a dental implant.

10. The implant according to claim 1, wherein each surface essentially has pores with diameter sizes in the range of 0.1-10 μm, and/or in that the total pore volume is within a range of $5\times10^{-2}$ and $10^{-5}$ cm$^3$.

11. The implant according to claim 1, wherein the titanium oxide layer has a thickness in the range of 2-20 μm.

12. The implant according to claim 1, wherein the titanium oxide layer is highly porous, with pore diameters in the range of 0.01-10 μm.

13. The implant according to claim 1, wherein the titanium oxide layer has a surface roughness of about 1-5 μm.

14. The implant according to claim 1, wherein the implant is a dental implant.

* * * * *